United States Patent
Berberich

[19]

[11] Patent Number: 6,084,417
[45] Date of Patent: *Jul. 4, 2000

[54] METHOD FOR DETERMINING THE MOISTURE IMPINGING ON A RESISTIVE RAIN SENSOR

[75] Inventor: Reinhold Berberich, Frankfurt, Germany

[73] Assignee: Mannesmann VDO AG, Frankfurt, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/555,639

[22] Filed: Nov. 8, 1995

[30] Foreign Application Priority Data

Nov. 9, 1994 [DE] Germany ............................. 44 39 717

[51] Int. Cl.$^7$ .................................................. G01N 27/07
[52] U.S. Cl. ........................ 324/711; 324/694; 318/483; 318/DIG. 2
[58] Field of Search ..................... 340/602, 604; 324/689, 694, 711; 116/69; 318/483, DIG. 2

[56] References Cited

U.S. PATENT DOCUMENTS

| | | | |
|---|---|---|---|
| 3,350,941 | 11/1967 | Misevich | 73/335 |
| 3,873,927 | 3/1975 | Overall | 328/4 |
| 3,882,381 | 5/1975 | Gregory | 324/61 R |
| 3,986,110 | 10/1976 | Overall | 324/61 R |
| 4,135,151 | 1/1979 | Rogers et al. | 324/61 |
| 4,137,931 | 2/1979 | Hasenbeck | 137/78 |
| 4,546,916 | 10/1985 | Tsuaki | 236/44 A |
| 4,793,182 | 12/1988 | Djorup | 73/336.5 |
| 4,916,374 | 4/1990 | Schierbeek | 318/483 |
| 5,486,815 | 1/1996 | Wagner | 340/602 |
| 5,546,974 | 8/1996 | Bireley | 137/78.3 |

*Primary Examiner*—Josie Ballato
*Assistant Examiner*—Jose M. Solis
*Attorney, Agent, or Firm*—Martin A. Farber

[57] ABSTRACT

In a method and a system for the operation of a resistive moisture sensor, conductance of the sensor is measured, whereby current through the moisture sensor is measured preferably during an application of a voltage to the moisture sensor. In order to avoid electrolytic phenomena, the voltage is fed to the moisture sensor via a capacitor, and has a waveform of two pulses of different polarity following shortly one after the other.

15 Claims, 1 Drawing Sheet

METHOD FOR DETERMINING THE MOISTURE IMPINGING ON A RESISTIVE RAIN SENSOR

FIELD AND BACKGROUND OF THE INVENTION

The present invention relates to a process and system for the operation of a resistive moisture sensor.

Resistive moisture sensors are used for instance in order to report moisture or raindrops on the windshield of a motor vehicle so as to control the windshield wiper automatically or semiautomatically. For this purpose, conductive paths are applied to the windshield or to some other suitable place so that the resistance between the conductive paths decreases with the amount of moisture present.

For evaluating this change in resistance, resistance measuring circuits have become known in which finally the voltage on the moisture sensor upon the presence of a predetermined current is measured.

In that case, there is an inversely proportional dependence between the voltage and the amount of moisture; in other words, for instance, a first drop to fall on a dry windshield produces a relatively large change in voltage while, if the windshield is already wet, a further drop results in only a smaller change.

SUMMARY OF THE INVENTION

However, since one is interested upon the evaluation of the signal of moisture-sensors in detecting additionally impinging moisture regardless of the existing degree of wetting of the moisture sensor, the object of the invention is to obtain a signal which, regardless of basic or residual moisture of the moisture sensor has a constantly large increase upon the new impingement of moisture.

This object is achieved with the method of the invention in the manner that the conductance of the sensor is measured. In this connection, it is preferable for the current through the moisture sensor to be measured during the application of a voltage to the moisture sensor.

By the method of the invention, a sensitivity of the moisture sensor is obtained which is substantially independent of the degree of wetting. If one assumes, for instance, that all drops impinging on the moisture sensor have the same conductance, then all drops—from the first up to for instance the 19th or 20th—result in the same increase in signal.

Another requirement made on moisture sensors is that electrolytic erosion of the conductive paths and corrosion of parts of the car body are to be avoided. This is advantageously achieved in a further development of the method of the invention, in the manner that the voltage present on the moisture sensor is an alternating voltage.

This further development is preferably obtained in the manner that the voltage on the sensor is only applied at times and that the sensor is connected to high resistance during the remaining time. In this connection, it has been found favorable if the two successive pulses together have a duration of about 1 ms, while an interval following this lasts for about 9 ms.

In another further development of the invention, a resistor is connected in parallel with the sensor, and an interruption in the feed lines to the sensor is recognized by the fact that the current measured is below a predetermined value.

One advantageous arrangement for carrying out the method of the invention provides that, in order to measure the current, a measurement resistor is connected in series with the moisture sensor and that the voltage drop over the measurement resistor can be fed, via an amplifier, to an analog-signal input of a microcomputer. In this connection, it is advantageous if the voltage acting on the sensor can be fed free of direct voltage over a capacitor.

In order to form the pulsed voltage, an output of the microcomputer can be connected, for a feeding of the voltage, to an input of a switchable amplifier the output of which is connected to a terminal of a capacitor which is connected in series with the moisture sensor. A further output of the microcomputer is connected to a control input of the switchable amplifier.

BRIEF DESCRIPTION OF THE DRAWINGS

With the above and other objects and other advantages in view, the present invention will become more clearly understood in connection with the detailed description of the preferred embodiment, when considered with the accompanying drawings of which.

DETAILED DESCRIPTION OF THE PREFERRED EMBODIMENTS

Figure 1:
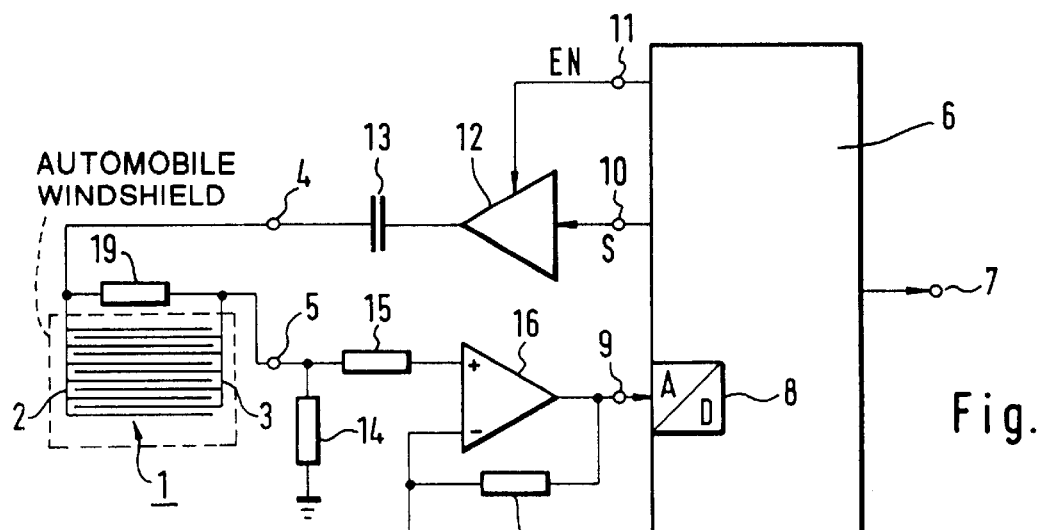
FIG. 1 is a block diagram of a system in accordance with the invention.

With reference to FIG. 1, a moisture sensor 1 consists of conductive paths which form two electrodes 2, 3 which are nested in each other and are connected via terminals 4, 5 to an evaluation circuit. The evaluation circuit contains a microcomputer 6, from the output 7 of which a signal which characterizes the moisture can be obtained. In addition to other elements, the microcomputer 6 contains an analog-to-digital converter 8 having an analog signal input 9. Signals are outputted from outputs 10, 11 of the microcomputer 6. In order to apply a pulsed voltage to the moisture sensor 1, a switchable amplifier 12 is provided, and has an output which is connected to a high resistance by means of a control input of the of the amplifier 12. This control input receives a signal EN from the output 11 of the microcomputer 6, while the signal input of the amplifier is connected to the output 10 which conducts a signal S. The output of the switchable amplifier 12 is connected via a capacitor 13 to the terminal 4 of the moisture sensor 1.

In order to measure the current through the moisture sensor 1, the terminal 5 is connected to ground potential via a measurement resistor 14. The voltage at the terminal 5 therefore corresponds to the current-proportional voltage drop over the measurement resistor 14 and is fed via a resistor 15 to the non-inverting input of a difference amplifier 16. Via a voltage divider comprising resistors 17 and 18, the inverting input of difference amplifier 16 receives a part of the output voltage of the difference amplifier 16. The degree of amplification is thus determined by the divider ratio. The output voltage of the difference amplifier 16 is fed to the analog-signal input 9 of the microcomputer 6.

Figure 2:
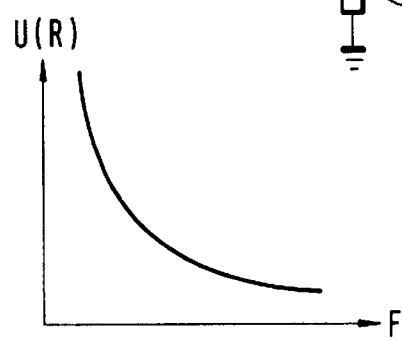
FIG. 2 shows the dependence of a resistance-proportional voltage obtained in accordance with the known methods on the amount of moisture.
Figure 3:
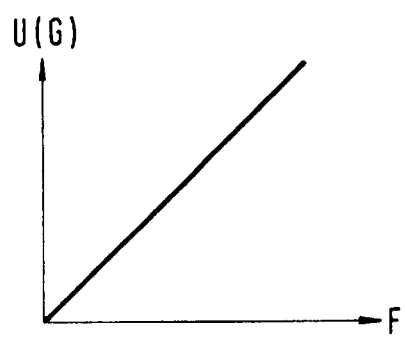
FIG. 3 shows the dependence of the voltage obtained with the method of the invention on the amount of moisture.

It can be seen from FIG. 2 that, with an increase in the number of drops which have already fallen on the moisture sensor given by the horizontal axis F, the dependence of the voltage U(R) on the number of drops becomes smaller. In contradistinction to this, in the method of the invention as shown in FIG. 3, each additional drop is perceptible with an equally large increase in the voltage U(G).

Figure 4:
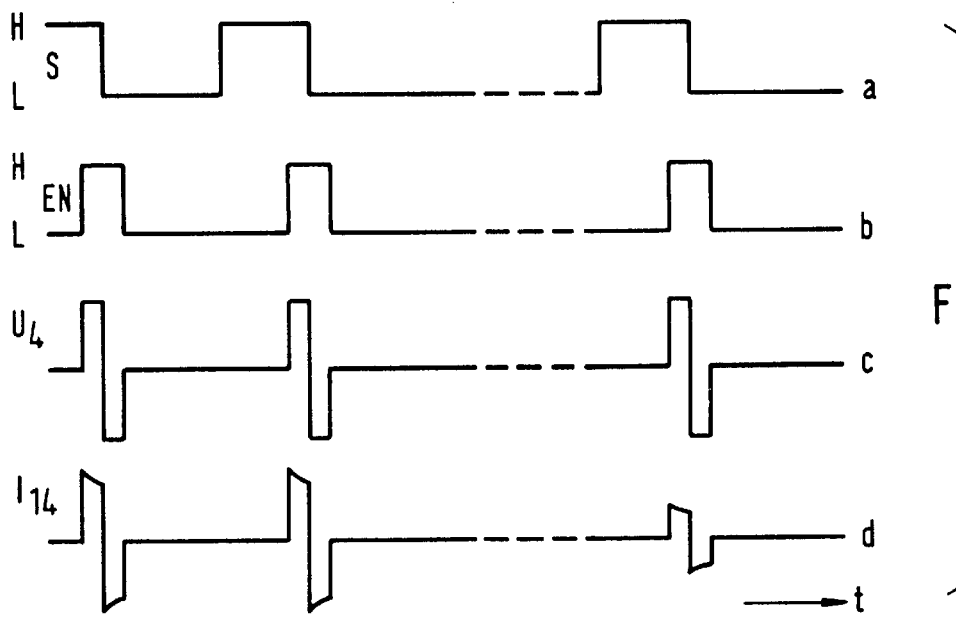
FIG. 4 shows the variation with time of the current through the moisture sensor.

FIG. 4 shows the course of the signals S and EN, of the voltage $U_4$ at the terminal 4 of the current $I_{14}$ through the measurement resistor 14. For the duration of the pair of pulses shown in lines c and d, the switchable amplifier 12 is connected by the signal EN (line b) so that during this time the signal S (line a) passes via the capacitor 13 to the terminal 4. The direct voltage component is suppressed by the capacitor 13 so that the voltage jump present in each case between the pulses of different polarity results. During the interval between the pairs of pulses, the switchable amplifier 12 is of high resistance so that the voltage (line c) remains initially at 0 even though the signal S jumps from L to H. Only when the signal EN again assumes the value H does the positive level arrive as positive flank of the next pair of pulses at the terminal 4.

The pulses of the current $I_{14}$ shown in line d show slight exponential-function-like top inclinations which, caused by shifts in charge in the fluid wetting the moisture sensor 1 are, however, not essential for the principle of the invention. In principle, the moisture sensor 1 has a conductivity which increases with the amount of moisture, so that the current $I_{14}$ also becomes greater with an increase in the amount of moisture. This is indicated in FIG. 4 in the manner that, to the left of the interruption, two pairs of pulses of the current $I_{14}$ are shown in the case of a larger amount of moisture, and to the right of the interruption, one pair of pulses is shown in the case of a smaller amount of moisture.

A resistor 19 connected between the terminals 4 and 5 has a two-fold function. On the one hand, it assures a slight flow of current through the measurement resistor 14 even when the sensor 1 is completely dry, whereby assurance is had that the amplifier 16 already receives an input voltage which is greater than its offset voltage even when the sensor is dry. The parallel combination of resistor 19 and the sensor 1 form a voltage divider with the resistor 14.

On the other hand, if the resistor 19 is located close to the sensor contacts, it can definitely be concluded that there is an interruption in the sensor feed line if a smaller current flows through the resistor 14 than that caused by the resistor 19.

The duration of the pairs of pulses and of the interval or the frequency of repetition can be selected in accordance with the particular circumstances, for instance the size of the moisture sensor. Values which can be used in practice are, for instance, a duration of 1 ms and an interval of about 9 ms.

I claim:

1. A method for the operation of a resistive sensor having electrodes disposed on a surface for measuring moisture thereon, wherein upon exposure of the electrodes to the environment, a change of resistance of the sensor results upon a deposition of the moisture on the sensor electrodes, the method comprising steps of:

connecting a first terminal of a measurement resistor directly to a first of said electrodes of said sensor;

applying voltage to resistive elements of the sensor, in the form of a sequence of pulses, between the sensor electrodes, said voltage being applied between a second of said electrodes of said sensor and a second terminal of said resistor and resulting in a flow of current through said measurement resistor in the presence of moisture on said sensor, the interconnection of said sensor to said measurement resistor providing for current flow within said sensor alone a single path of current flow between said second electrode of said sensor and said second terminal of said resistor;

inhibiting corrosion of the sensor by generating the pulses in the sequence of the pulses with alternating polarity of voltage; and measuring conductance of the sensor, wherein said measuring step includes a measuring of voltage drop across said measurement resistor for improved linearity of measurement, and utilizing a continuous variation in magnitude of said voltage drop as a measure of continuous variation in magnitude of said conductance.

2. A method according to claim 1, wherein, in said measuring step, a current through the moisture sensor is measured during application of the voltage to the moisture sensor.

3. A method according to claim 2, wherein, in said voltage applying step, the voltage present on the moisture sensor is an alternating voltage.

4. A method according to claim 3, wherein in said voltage applying step, there is an applying of the voltage on the sensor only during a plurality of time intervals, there being a further step of connecting the sensor to a high resistance during times between said time intervals.

5. A method according to claim 4, wherein the alternating voltage fed to the sensor in a first of said time intervals consists of two pulses of varying polarity which follow one after the other.

6. A method according to claim 5, wherein the two pulses which follow one after the other in said first time interval together have a duration of approximately 1 ms, while a period of time between successive ones of said time intervals lasts approximately 9 ms.

7. A method according to claim 1, further comprising a step of:

connecting a resistor in parallel with the sensor; and recognizing that an interruption in feed lines to the sensor is present;

wherein said recognizing step comprises steps of measuring current flow through the parallel circuit of resistor and sensor; and determining that the current measured is below a predetermined value.

8. A method for operating a moisture sensor having plural electrodes disposed on a surface for measuring moisture thereon, wherein upon exposure of the surface to the environment, a change of resistance of the sensor results in response to a deposition of moisture on the sensor electrodes, the sensor having terminals connecting with respective ones of the electrodes, the method comprising steps of:

providing a resistance voltage divider comprising a first resistor having first and second terminals, and a second resistor having first and second terminals serially connected to the first resistor, wherein the first terminal of said first resistor connects with the first terminal of said second resistor;

connecting the sensor, by its terminals, in parallel to the first resistor to provide a first circuit element wherein a first and a second electrode of said sensor are connected directly and respectively to the first and the second terminal of said first resistor;

applying a drive voltage across the resistance voltage divider between the second terminal of said first resistor and the second terminal of said second resistor; and measuring a signal voltage across the second resistor for improved linearity of measurement, a magnitude of the signal voltage increasing substantially linearly with an increase in an amount of wetness upon the surface;

wherein the interconnection of said circuit element to said second resistor provides for current flow within said sensor along a single path of current flow between a second electrode of said sensor and a second terminal of said second resistor; and said measuring step includes utilizing a continuous variation in magnitude of said signal voltage as a measure of a continuous variation in magnitude of a conductance of said sensor.

9. A method according to claim 8, wherein the drive voltage comprises a sequence of voltage pulses.

10. A method according to claim 9, wherein, in the drive voltage, the pulses of the sequence of pulses have alternating polarity to inhibit corrosion of the sensor.

11. A method according to claim 8, wherein, in said step of connecting the sensor in parallel with the first resistor includes a step of locating said first resistor near said sensor terminals.

12. A method according to claim 8, wherein:

in said voltage applying step, said voltage is provided by a source of voltage in the form of a sequence of unidirectional pulses, there being a further step of coupling a capacitor between said voltage source and said voltage divider to convert said unidirectional pulses to bidirectional pulses.

13. A method according to claim 12, further comprising a step of generating said pulses spaced apart in time such that the interpulse interval between successive ones of said pulses is greater than the duration of an individual one of said pulses by a factor of approximately an order of magnitude.

14. A method according to clam 13, wherein said factor is approximately 9, and the pulse duration is approximately one millisecond.

15. A method according to claim 8, further comprising a step of generating said pulses spaced apart in time such that the interpulse interval between successive ones of said pulses is greater than the duration of an individual one of said pulses by a factor of approximately an order of magnitude.

* * * * *